United States Patent
Takeuchi et al.

(10) Patent No.: US 8,889,594 B2
(45) Date of Patent: *Nov. 18, 2014

(54) AGENT FOR IMPROVING GOOD RICE SEEDLING GROWTH

(75) Inventors: Yasutomo Takeuchi, Utsunomiya (JP); Shigeyuki Funada, Satte (JP)

(73) Assignee: Cosmo Oil Co., Ltd., Tokyo (JP)

(*) Notice: Subject to any disclaimer, the term of this patent is extended or adjusted under 35 U.S.C. 154(b) by 474 days.

This patent is subject to a terminal disclaimer.

(21) Appl. No.: 12/866,150

(22) PCT Filed: Mar. 26, 2009

(86) PCT No.: PCT/JP2009/001349
§ 371 (c)(1),
(2), (4) Date: Aug. 4, 2010

(87) PCT Pub. No.: WO2009/139105
PCT Pub. Date: Nov. 19, 2009

(65) Prior Publication Data
US 2010/0331183 A1 Dec. 30, 2010

(30) Foreign Application Priority Data
May 13, 2008 (JP) ................. 2008-126017

(51) Int. Cl.
*A01N 37/44* (2006.01)
*A01N 37/00* (2006.01)
*A01N 37/10* (2006.01)
*A01N 43/00* (2006.01)
*A01N 43/653* (2006.01)
*A01N 43/48* (2006.01)
*A01N 47/10* (2006.01)
*A01N 53/00* (2006.01)
*A01N 43/64* (2006.01)

(52) U.S. Cl.
CPC .................... *A01N 37/44* (2013.01)
USPC ........ 504/147; 504/139; 504/144; 504/174; 504/181; 504/182; 504/272; 504/313; 504/320; 514/561; 514/383; 514/531; 514/557

(58) Field of Classification Search
CPC ....... A01N 37/44; A01N 37/42; A01N 43/40; A01N 43/54; A01N 43/653; A01N 2300/00
USPC ......... 504/436, 272, 320, 147, 139, 144, 174, 504/181, 182, 313; 514/666, 561, 383, 531, 514/557
See application file for complete search history.

(56) References Cited

U.S. PATENT DOCUMENTS 5,298,482 A 3/1994 Tanaka et al.

FOREIGN PATENT DOCUMENTS

| CN | 1402976 | 3/2003 |
|---|---|---|
| JP | 61 212504 | 9/1986 |
| JP | 4 338305 | 11/1992 |
| JP | 2000 135032 | 5/2000 |

OTHER PUBLICATIONS

Wilhelm Rademacher, "Growth Retardants: Effects on Gibberellin Biosynthesis and OtherMetabolic Pathways", Annual Reviews of Plant Physiology and Plant Molecular Biology, 2000, 51:501-531.*
Sekimoto, Hitoshi "Suito Chijobu no Keishitsu ni Taisuru Gibberellin Seigosei Sogaizai no Sayo", Chemical Regulation of Plants, vol. 30, No. 1, pp. 92-96, ISSN: 0388-9130, (1995), (with English translation).
Fukui-Ken, "Growth of Healthy Seedlings Using Uniconazole P Liquid Preparation", Technology Transferred With Dissemination in Year (2005), (with partial English translation).
Kazuya, Iwai et al., "Recovering effect of trace-element fertilizer containing 5-aminolevulinic acid (ALA) on the growth-delay of sugar beet seedlings caused by uniconazoole", Proceedings of the Japanese Society for Chemical Regulation of Plants, No. 38, p. 71, (Oct. 10, 2003), (with English abstract).
International Search Report issued Apr. 21, 2009 in PCT/JP09/01349 filed Mar. 26, 2009.
U.S. Appl. No. 12/866,113, filed Aug. 4, 2010, Takeuchi, et al.
Office Action issued Dec. 5, 2012, in Chinese patent application No. 200980109244.0.

* cited by examiner

*Primary Examiner* — Abigail Fisher
*Assistant Examiner* — Nathan W Schlientz
(74) *Attorney, Agent, or Firm* — Oblon, Spivak, McClelland, Maier & Neustadt, L.L.P.

(57) ABSTRACT

There is provided an agent for improving the growth of seedlings, having effects of raising healthy rice seedlings, such as increase of the tillering number, increase of root weight, enhancement of greenness, and increase of stem thickness.
An agent for improving the growth of rice seedlings containing, as active ingredients, 5-aminolevulinic acid represented by formula (1), a derivative thereof or a salt of the acid or the derivative, and a gibberellin biosynthesis inhibitor:

$$R^2R^1NCH_2COCH_2CH_2COR^3 \quad (1)$$

wherein $R^1$ and $R^2$ each independently represent a hydrogen atom, an alkyl group, an acyl group, an alkoxycarbonyl group, an aryl group or an aralkyl group; and $R^3$ represents a hydroxyl group, an alkoxy group, an acyloxy group, an alkoxycarbonyloxy group, an aryloxy group, an aralkyloxy group or an amino group.

15 Claims, No Drawings

AGENT FOR IMPROVING GOOD RICE SEEDLING GROWTH

FIELD OF THE INVENTION

The present invention relates to an agent for improving the growth of rice seedlings.

BACKGROUND OF THE INVENTION

An important factor in the raising of rice seedlings, in which young plants that are susceptible to environmental changes or diseases and pests, are grown together under management, and seedlings that have grown to a certain extent are planted in the field, is to produce seedlings that are excellent in the growth of roots, stem thickness, dry weight and the degree of sturdiness (dry weight/height) and have a seedling height (or an internode) of an appropriate length.

Many agents for improving the growth of rice seedlings have been hitherto investigated. Hydroxyisoxazoles are known to have an effect of promoting root growth, and are thus used in the raising of healthy seedlings (Patent Document 1). Furthermore, there have been reports on the effect of seedling growth exerted by jasmonic acid, which is a plant hormone (Patent Document 2); the effect of seedling growth obtained by preventing turion formation using uniconazole P, which is a gibberellin biosynthesis inhibitor (Non-Patent Document 1); and the like.

However, these agents for improving the growth of the seedlings are still not fully satisfactory.

Meanwhile, 5-aminolevulinic acid, derivatives thereof, or salts of the acid or the derivatives exhibit an enhancement of photosynthetic activity, an enhancement of $CO_2$ absorption capability, an action of suppressing respiration, an action of enhancing the chlorophyll content, and also an excellent action of promoting growth. As a result, the compounds are known to show excellent effects in the promotion of root generation, prevention of lodging, increase of the yield, enhancement of cold hardiness, retainment of freshness, enhancement of greenness, retainment of greenness, raising of healthy seedlings, promotion of organ development, increase of the tillering number, shortening of the time period required for growth, alleviation of harmful side effects of chemicals, or increase of survival upon cutting and the like (Patent Document 3).

Furthermore, it has reported that when a young sugar beet plant is treated with uniconazole P, which is a gibberellin biosynthesis inhibitor, and then is treated with 5-aminolevulinic acid, a derivative thereof or a salt thereof, the growth of sugar beet can be induced (Non-Patent Document 2). This is a technology dealing with the problem that growth stagnation of sugar beet occurs, which means a decrease in the dry weight of sugar beet, as a result of sustainment of the effect of uniconazole P used for preventing turion formation, and solving the problem by increasing the dry weight due to the growth promoting effect of 5-aminolevulinic acid and returning to healthy growth, by treating sugar beet with 5-aminolevulinic acid 15 days after treatment with uniconazole P.

However, what becomes potent when uniconazole P and 5-aminolevulinic acid are used in combination, is the effect of preventing lodging of young sugar beet plants, which results from the summation of the effect of the gibberellin biosynthesis inhibitor inducing the suppression of internode elongation, and the effect of 5-aminolevulinic acid inducing repletion of roots and stems, and the growth effect of the seedlings is still not fully satisfactory.

Patent Document 1: JP-A-60-52048
Patent Document 2: JP-A-10-310580
Patent Document 3: JP-A-4-338305
Non-Patent Document 1: "Growth of Healthy Seedlings Using Uniconazole P Liquid Preparation", Technology transferred with dissemination in year 2005, Fukui-ken
Non-Patent Document 2: "Effect of Fertilizer Containing 5-Aminolevulinic Acid on Delay of Growth Due to Uniconazole Treatment", Proceedings of the Japanese Society for Chemical Regulation of Plants, No. 38, p. 71

SUMMARY OF THE INVENTION

Problem to be Solved by the Invention

Therefore, an object of the present invention is to provide an agent for improving the growth of rice seedlings, which has growth effects of healthy rice seedlings, such as increase of the tillering number, increase of root weight, enhancement of greenness, and increase of stem thickness.

Means for Solving Problem

The inventors of the present invention made a thorough investigation under such circumstances, and they found that when rice seedlings are treated with a gibberellin biosynthesis inhibitor causing growth inhibition, and with 5-aminolevulinic acid, a derivative thereof or a salt thereof, each having a growth promoting effect, the results are unexpectedly completely different from the instance of young sugar beet plants, and the inventors found new growth effects of the healthy rice seedlings, such as increase of the tillering number, increase of root weight, enhancement of greenness, and increase of stem thickness.

That is, the present invention provides an agent for improving the growth of rice seedling containing, as active ingredients, 5-aminolevulinic acid represented by formula (1), a derivative thereof or a salt of the acid or the derivative, and a gibberellin biosynthesis inhibitor:

$$R^2R^1NCH_2COCH_2CH_2COR^3 \qquad (1)$$

wherein $R^1$ and $R^2$ each independently represent a hydrogen atom, an alkyl group, an acyl group, an alkoxycarbonyl group, an aryl group or an aralkyl group; and $R^3$ represents a hydroxyl group, an alkoxy group, an acyloxy group, an alkoxycarbonyloxy group, an aryloxy group, an aralkyloxy group or an amino group.

The present invention also provides the use of a composition containing 5-aminolevulinic acid represented by the formula (1), a derivative thereof or a salt of the acid or the derivative, and a gibberellin biosynthesis inhibitor, as an agent for improving the growth of rice seedling.

Furthermore, the present invention provides a method for enhancing the growth of rice seedling, the method including treating rice with 5-aminolevulinic acid represented by the formula (1), a derivative thereof or a salt of the acid or the derivative, and a gibberellin biosynthesis inhibitor.

EFFECT OF THE INVENTION

The agent for improving the growth of rice seedling of the present invention has growth effects of rice seedlings, such as increase of the tillering number, increase of root weight, enhancement of greenness, and increase of stem thickness.

DETAILED DESCRIPTION OF THE INVENTION

One of the active ingredients of the agent for improving the growth of seedling of the present invention includes 5-aminolevulinic acid, a derivative thereof (the formula (1)), or a salt of the acid or the derivative.

In the formula (1), the alkyl group represented by $R^1$ and $R^2$ is preferably a straight-chained or branched alkyl group having 1 to 24 carbon atoms, more preferably an alkyl group having 1 to 18 carbon atoms, and particularly preferably an alkyl group having 1 to 6 carbon atoms. Examples of the alkyl group having 1 to 6 carbon atoms include a methyl group, an ethyl group, an n-propyl group, an isopropyl group, an n-butyl group, and a sec-butyl group. The acyl group is preferably a straight-chained or branched alkanoyl group, alkenylcarbonyl group or aroyl group, each having 1 to 12 carbon atoms, and is particularly preferably an alkanoyl group having 1 to 6 carbon atoms. Examples of the acyl group include a formyl group, an acetyl group, a propionyl group, and a butyryl group. The alkoxycarbonyl group is preferably an alkoxycarbonyl group having 2 to 13 carbon atoms in total, and particularly preferably an alkoxycarbonyl group having 2 to 7 carbon atoms. Examples of the alkoxycarbonyl group include a methoxycarbonyl group, an ethoxycarbonyl group, an n-propoxycarbonyl group, and an isopropoxycarbonyl group. The aryl group is preferably an aryl group having 6 to 16 carbon atoms, and examples thereof include a phenyl group, and a naphthyl group. The aralkyl group is preferably a group formed from an aryl group having 6 to 16 carbon atoms and an alkyl group having 1 to 6 carbon atoms, and examples thereof include a benzyl group.

The alkoxy group represented by $R^3$ is preferably a straight-chained or branched alkoxy group having 1 to 24 carbon atoms, more preferably an alkoxy group having 1 to 16 carbon atoms, and particularly preferably an alkoxy group having 1 to 12 carbon atoms. Examples of the alkoxy group include a methoxy group, an ethoxy group, an n-propoxy group, an isopropoxy group, an n-butoxy group, a pentyloxy group, a hexyloxy group, an octyloxy group, a decyloxy group, a dodecyloxy group, and the like. The acyloxy group is preferably a straight-chained or branched alkanoyloxy group having 1 to 12 carbon atoms, and particularly preferably an alkanoyloxy group having 1 to 6 carbon atoms. Examples of the acyloxy group include an acetoxy group, a propionyloxy group, and a butyryloxy group. The alkoxycarbonyloxy group is preferably an alkoxycarbonyloxy group having 2 to 13 carbon atoms in total, and particularly preferably an alkoxycarbonyloxy group having 2 to 7 carbon atoms in total. Examples of the alkoxycarbonyloxy group include a methoxycarbonyloxy group, an ethoxycarbonyloxy group, an n-propoxycarbonyloxy group, and an isopropoxycarbonyloxy group. The aryloxy group is preferably an aryloxy group having 6 to 16 carbon atoms, and examples thereof include a phenoxy group, and a naphthyloxy group. The aralkyloxy group is preferably a group having the aralkyl group mentioned above, and examples thereof include a benzyloxy group.

In the formula (1), $R^1$ and $R^2$ are each preferably a hydrogen atom. $R^3$ is preferably a hydroxyl group, an alkoxy group or an aralkyloxy group, more preferably a hydroxyl group or an alkoxy group having 1 to 12 carbon atoms, and particularly preferably a methoxy group or a hexyloxy group.

Examples of the 5-aminolevulinic acid derivatives include 5-aminolevulinic acid methyl ester, 5-aminolevulinic acid ethyl ester, 5-aminolevulinic acid propyl ester, 5-aminolevulinic acid butyl ester, 5-aminolevulinic acid pentyl ester, 5-aminolevulinic acid hexyl ester, and the like. Particularly, 5-aminolevulinic acid methyl ester or 5-aminolevulinic acid hexyl ester is preferred.

Examples of the salts of 5-aminolevulinic acid and its derivatives include acid addition salts such as hydrochloride, phosphate, nitrate, sulfate, sulfonate, acetate, propionate, butyrate, valerate, citrate, fumarate, maleate and malate; and metal salts such as sodium salt, potassium salt and calcium salt. 5-Aminolevulinic acid and salts thereof can be used singly, or as mixtures of two or more of these.

5-aminolevulinic acid, derivatives thereof, or salts of the acid or the derivatives can be produced according to any of chemical syntheses, and methods utilizing microorganisms or enzymes. For example, the methods described in JP-A-4-9360, JP-T-11-501914, Japanese Patent Application No. 2004-99670, Japanese Patent Application No. 2004-99671, and Japanese Patent Application No. 2004-99672 may be mentioned. Products thereof can be used directly without going through separation and purification, as long as the products do not contain substances that are harmful to rice. If the products contain any harmful substances, the products can be used after eliminating the harmful substances appropriately to a level that is not regarded as harmful.

Examples of the gibberellin biosynthesis inhibitor, which is one of the active ingredients in the agent for improving the growth of rice seedling of the present invention, include inabenfide (4'-chloro-2'-α-hydroxybenzyl)isonicotinanilide), uniconazole P ((E)-(S)-1-(4-chlorophenyl)-4,4-dimethyl-2-(1H-1,2,4-triazol-1-yl)pent-1-en-3-ol), trinexapac-ethyl (ethyl=4-cyclopropyl-α-hydroxymethylene)-3,5-dioxocyclohexane carboxylate), paclobutrazol ((2RS,3RS)-1-(4-chlorophenyl)-4,4-dimethyl-2-(1H-1,2,4-triazol-1-yl)pentan-3-ol), prohexadione calcium salt (calcium 3-oxido-5-oxo-4-propionyl-3-cyclohexene carboxylate), flurprimidol (2-methyl-pyrimidin-5-yl-1-(4-trifluoromethoxyphenyl) propan-1-ol), ancymidol (α-cyclopropyl-α(4-methoxyphenyl)-5-pyrimidinemethanol), chlormequat (2-chloroethyltrimethylammonium=chloride), and daminozide (N-(dimethylamino)succinamide acid). Among these, inabenfide, uniconazole P, trinexapac-ethyl, paclobutrazol, prohexadione calcium salt and flurprimidol, which are excellent in the effect of growing seedlings when used in combination with 5-aminolevulinic acid, derivatives thereof or salts of the acid or the derivatives, are more preferred, and particularly, inabenfide, trinexapac-ethyl and paclobutrazol are preferred.

The plants which are the targets of application of the agent for improving the growth of seedlings according to the present invention, are preferably the japonica species and the indica species, and more preferably the japonica species.

According to the present invention, it is acceptable if the agent for improving the growth of rice seedlings contains 5-aminolevulinic acid, a derivative thereof or a salt of the acid or the derivative, and a gibberellin biosynthesis inhibitor, but the agent can be further incorporated with, if necessary, plant growth regulators, sugars, amino acids, organic acids, alcohols, vitamins, minerals and the like, in addition to the those ingredients.

Examples of the plant growth regulators used herein include brassinolides such as epibrassinolides; choline preparations such as choline chloride and choline nitrate; indolebutyric acid, indoleacetic acid, ethyclozate preparations, 1-naphthylacetamide preparations, isoprothiolane preparations, nicotinic acid amide preparations, hydroxyisoxazole preparations, calcium peroxide preparations, benzylaminopurine preparations, methasulfocarb preparations, oxyethylene docosanol preparations, ethephon preparations, cloxyfonac preparations, gibberellins, streptomycin preparations, daminozide preparations, benzylaminopurine preparations, 4-CPA preparations, ancymidol preparations, inabenfide preparations, chlormequat preparations, dikegulac preparations, mefluidide preparations, calcium carbonate preparations, and piperonyl butoxide preparations.

Examples of the sugars include glucose, sucrose, xylytol, sorbitol, galactose, xylose, mannose, arabinose, madulose, sucrose, ribose, rhamnose, fructose, maltose, lactose, and maltotriose.

Examples of the amino acids include asparagine, glutamine, histidine, tyrosine, glycine, arginine, alanine, tryptophan, methionine, valine, proline, leucine, lysine, and isoleucine.

Examples of the organic acids include formic acid, acetic acid, propionic acid, butyric acid, valeric acid, oxalic acid, phthalic acid, benzoic acid, lactic acid, citric acid, tartaric acid, malonic acid, malic acid, succinic acid, glycolic acid, glutamic acid, aspartic acid, maleic acid, caproic acid, caprylic acid, myristic acid, stearic acid, palmitic acid, pyruvic acid, α-ketoglutaric acid, and levulinic acid.

Examples of the alcohols include methanol, ethanol, propanol, butanol, pentanol, hexanol, and glycerol.

Examples of the vitamins include nicotinic acid amide, vitamin $B_6$, vitamin $B_{12}$, vitamin $B_5$, vitamin C, vitamin $B_{13}$, vitamin $B_1$, vitamin $B_3$, vitamin $B_2$, vitamin $K_3$, vitamin A, vitamin $D_2$, vitamin $D_3$, vitamin $K_1$, α-tocopherol, β-tocopherol, γ-tocopherol, σ-tocopherol, p-hydroxybenzoic acid, biotin, folic acid, nicotinic acid, pantothenic acid, and α-liponic acid.

Examples of the minerals include nitrogen, phosphorus, potassium, calcium, boron, manganese, magnesium, zinc, copper, iron, molybdenum, and magnesium.

The agent for improving the growth of rice seedlings of the present invention is put to use by administering to the roots or the stems and leaves of the plant, or to the soil and water in the surroundings. The agent may be in the form of a solid or may be in the form of an aqueous solution, at the time of administration. Specifically, the agent may be used for foliage treatment (foliage treatment agent) or may also be used for soil treatment (soil treatment agent).

The amount ratio of 5-aminolevulinic acid, a derivative thereof or a salt of the acid or the derivative to the gibberellin biosynthesis inhibitor, which are both active ingredients of the agent for improving the growth of rice seedling, is such that relative to 100 parts by weight of 5-aminolevulinic acid, a derivative thereof or a salt of the acid or the derivative, 60 to 6,000,000 parts by weight of the gibberellin biosynthesis inhibitor is preferred, and 300 to 1,200,000 parts by weight of the inhibitor is more preferred, while 600 to 600,000 parts by weight of the inhibitor is particularly preferred. However, it is preferable to appropriately determine the weight ratio in accordance with the type of the gibberellin biosynthesis inhibitor used.

Specifically, in the treatment of rice with the agent for improving the growth of rice seedlings, it is preferable to use the agent in an amount of 0.1 to 10,000 mg, particularly preferably 1 to 2,000 mg, and more preferably 1 to 1,000 mg, in terms of 5-aminolevulinic acid, a derivative thereof or a salt of the acid or the derivative, per 10 ares. The amount of treatment of the gibberellin biosynthesis inhibitor may vary depending on the type of the inhibitor, but it is preferable to use the inhibitor in an amount of 0.1 to 12,000 g, and more preferably 0.625 to 2,400 g, per 10 ares. Specifically, the amount of treatment of inabenfide is preferably 120 to 12,000 g, and more preferably 600 to 2,400 g, per 10 ares. Similarly, the amount of treatment of uniconazole P is preferably 3 to 300 g, and more preferably 15 to 60 g, per 10 ares, and the amount of treatment of trinexapac-ethyl is preferably 0.125 to 12.5 g, and more preferably 0.625 to 2.5 g, per 10 ares. The amount of treatment of paclobutrazol is preferably 9 to 900 g, and more preferably 36 to 180 g, per 10 ares, and the amount of treatment of prohexadione calcium salt is preferably 1.5 g to 150 g, and more preferably 7.5 to 30 g, per 10 ares.

Furthermore, it is preferable to treat rice with a preparation prepared to give the amount of treatment in the range described above, in an amount of 10 to 1,000 L, and more preferably 20 to 300 L, per 10 ares.

In the case of using the agent as a foliage treatment agent, the type of the spreading agent and the amount of use are not particularly limited.

In regard to the timing for the treatment of plants with the agent for improving the growth of rice seedlings, when the agent is used in the growth of rice seedlings, a good time may be the period of raising seedlings before carrying out transplantation of rice seedlings to the paddy field.

The treatment using 5-aminolevulinic acid, a derivative thereof or a salt of the acid or the derivative, and the treatment using a gibberellin biosynthesis inhibitor, which components are the active ingredients of the present invention, are preferably carried out simultaneously, and it is more preferable to carry out the treatment using a mixture of the two components. However, the mode of treatment is not limited to these, as long as the respective effects of the active ingredients are manifested.

In the case of carrying out the treatment using 5-aminolevulinic acid, a derivative thereof or a salt of the acid or the derivative, and the treatment using a gibberellin biosynthesis inhibitor, which components are the active ingredients of the subject agent, at different times, it is preferable to first carry out the treatment using any one component and then to carry out the treatment using the other one component within 10 days, and more preferably within 5 days.

EXAMPLES

Hereinafter, the present invention will be described in more detail by way of Examples, but the present invention is not intended to be limited to these.

Example 1

Effect of Improving the Growth of Rice Seedlings—1

450 g/pot of soil was placed in a seedling box (the area was 1/120,000×10 a). The soil used was a purchased volcanic ash soil (andosol). Rice seeds (of koshihikari variety) which had been subjected to brine grading using a brine having a specific gravity of 1.13, and had been germinated, were sowed at a rate of 15 seeds/pot, and the seeds were covered with soil at a depth of 1 to 2 cm (50 g/pot). Fertilizer application was carried out using a liquid fertilizer, Hyponica, at a rate of 3 kg-N/10 a. For each of the test zones (n=4), the soil was irrigated with combinations of uniconazole P, inabenfide, trinexapac-ethyl, prohexadione calcium salt, paclobutrazol and 5-aminolevulinic acid hydrochloride, in a liquid amount of 200 L/10 a, so as to meet the final amount of treatment as indicated in Table 1. After 29 days from sowing, additional fertilizer application was carried out using a liquid fertilizer, Hyponica, at a rate of 3 kg-N/10 a. After 33 days from sowing, the plant bodies were harvested, and the fresh weight (roots) and the tillering number were measured. The effects obtained with 5-aminolevulinic acid hydrochloride and uniconazole P are presented in Table 1, and the effects obtained with 5-aminolevulinic acid hydrochloride and inabenfide, trinexapac-ethyl, prohexadione calcium salt or paclobutrazol are presented in Tables 2 to 5, respectively.

TABLE 1

Effects of 5-aminolevulinic acid hydrochloride and uniconazole P on rice seedling-growth

| Concentration of 5-aminolevulinic acid hydrochloride (mg/10 a) | Gibberellin biosynthesis inhibitor and treatment concentration (g/10 a) | Fresh weight of roots (g) | Average tillering number per plant body |
|---|---|---|---|
| 0 | 0 | 0.29 | 0.00 |
| 200 | 0 | 0.29 | 0.00 |
| 0 | Uniconazole P 30 | 0.28 | 0.86 |
| 200 | Uniconazole P 30 | 0.36 | 0.97 |

TABLE 2

Effects of 5-aminolevulinic acid hydrochloride and inabenfide on rice seedling-growth

| Concentration of 5-aminolevulinic acid hydrochloride (mg/10 a) | Gibberellin biosynthesis inhibitor and treatment concentration (g/10 a) | Fresh weight of roots (g) | Average tillering number per plant body |
|---|---|---|---|
| 0 | 0 | 0.29 | 0.00 |
| 200 | 0 | 0.29 | 0.00 |
| 0 | Inabenfide 1200 | 0.34 | 0.19 |
| 200 | Inabenfide 1200 | 0.39 | 0.37 |

TABLE 3

Effects of 5-aminolevulinic acid hydrochloride and trinexapac-ethyl on rice seedling-growth

| Concentration of 5-aminolevulinic acid hydrochloride (mg/10 a) | Gibberellin biosynthesis inhibitor and treatment concentration (g/10 a) | Fresh weight of roots (g) | Average tillering number per plant body |
|---|---|---|---|
| 0 | 0 | 0.29 | 0.00 |
| 200 | 0 | 0.29 | 0.00 |
| 0 | Trinexapac-ethyl 1.25 | 0.23 | 0.00 |
| 200 | Trinexapac-ethyl 1.25 | 0.34 | 0.06 |

TABLE 4

Effects of 5-aminolevulinic acid hydrochloride and prohexadione calcium salt on rice seedling-growth

| Concentration of 5-aminolevulinic acid hydrochloride (mg/10 a) | Gibberellin biosynthesis inhibitor and treatment concentration (g/10 a) | Fresh weight of roots (g) |
|---|---|---|
| 0 | 0 | 0.29 |
| 200 | 0 | 0.29 |
| 0 | Prohexadione calcium salt 15 | 0.32 |
| 200 | Prohexadione calcium salt 15 | 0.36 |

TABLE 5

Rice seedling-growth effects of 5-aminolevulinic acid hydrochloride and paclobutrazol

| Concentration of 5-aminolevulinic acid hydrochloride (mg/10 a) | Gibberellin biosynthesis inhibitor and treatment concentration (g/10 a) | Fresh weight of roots (g) | Average tillering number per plant body |
|---|---|---|---|
| 0 | 0 | 0.29 | 0.00 |
| 200 | 0 | 0.29 | 0.00 |
| 0 | paclobutrazol 90 | 0.29 | 0.80 |
| 200 | paclobutrazol 90 | 0.38 | 0.99 |

As shown in Tables 1 to 5, an effect of improving rice seedling growth that was surpassing the summation of effects, was recognized when 5-aminolevulinic acid hydrochloride and the gibberellin biosynthesis inhibitor were used in combination, as compared to the case where the components were used individually. Thus, it was found that a combination of these components was useful as an agent for improving seedling growth.

Example 2

Effect of Improving Rice Seedling Growth—2

450 g/pot of soil was placed in a seedling box (the area was 1/120,000×10 a). The soil used was a purchased volcanic ash soil (andosol). Rice seeds which had been subjected to brine grading using a brine having a specific gravity of 1.13, and had been germinated, were sowed at a rate of 15 seeds/pot, and the seeds were covered with soil at a depth of 1 to 2 cm (50 g/pot). Fertilizer application was carried out using a liquid fertilizer, Hyponica, at a rate of 5 kg-N/10 a. For each of the test zones (n=4), the soil was irrigated with combinations of inabenfide in an amount of treatment of 1,200 or 300 g/10 a, and 5-aminolevulinic acid hydrochloride in an amount of treatment of 600, 200 or 120 mg/10 a. After 22 days from sowing, the plant bodies were harvested, and the fresh weight (roots), the tillering number, the stem thickness and the chlorophyll content (SPAD value) were measured. The results for the fresh weight of roots and the tillering number under various conditions are presented in Table 6, and the results for the stem thickness and the chlorophyll content (SPAD value) under various conditions are presented in Table 7.

TABLE 6

Fresh weight of roots and average tillering number obtained by treatment of rice seedlings with 5-aminolevulinic acid hydrochloride and inabenfide

| Concentration of 5-aminolevulinic acid hydrochloride (mg/10 a) | Treatment concentration of inabenfide (g/10 a) | Fresh weight of roots (g) | Average tillering number per plant body |
|---|---|---|---|
| 0 | 0 | 0.34 | 0.03 |
| 120 | 0 | 0.35 | 0.03 |
| 200 | 0 | 0.36 | 0.01 |
| 600 | 0 | 0.35 | 0.00 |
| 0 | 300 | 0.35 | 0.11 |
| 200 | 300 | 0.36 | 0.22 |
| 0 | 1200 | 0.35 | 0.41 |
| 120 | 1200 | 0.36 | 0.49 |
| 200 | 1200 | 0.40 | 0.78 |

For the fresh weight of roots and the tillering number, n = 65 to 70

As shown in Table 6, it was recognized that the fresh weight of roots and the average tillering number increased to values that were surpassing their summation, when 5-aminolevulinic acid hydrochloride and inabenfide, which is a gibberellin biosynthesis inhibitor, were used in combination, as compared to the case where the components were used individually. Thus, it was found that a combination of these components was useful as an agent for improving seedling growth.

TABLE 7

Stem thickness and chlorophyll content obtained by treatment of rice seedlings with 5-aminolevulinic acid hydrochloride and inabenfide

| Concentration of 5-aminolevulinic acid hydrochloride (mg/10 a) | Treatment concentration of inabenfide (g/10 a) | Stem thickness (cm) | SPAD value |
|---|---|---|---|
| 0 | 0 | 0.409 | 27.36 |
| 600 | 0 | 0.429 | 28.70 |
| 0 | 300 | 0.415 | 29.23 |
| 600 | 300 | 0.479 | 32.59 |

For the stem thickness and the SPAD value, n = 15 to 17

As shown in Table 7, it was recognized that the stem thickness and the chlorophyll content increased to values that were surpassing their summation, when 5-aminolevulinic acid hydrochloride and inabenfide, which is a gibberellin biosynthesis inhibitor, were used in combination, as compared to the case where the components were used individually. Thus, it was found that a combination of these components was useful as an agent for improving seedling growth.

Example 3

Verification of Effect of Improving the Growth of Rice Seedlings

Seedlings were raised in the same manner as in Example 2. In regard to the treatment concentration upon raising seedlings, the treatment was carried out using 5-aminolevulinic acid hydrochloride at a concentration of 120 (mg/10 a) and inabenfide at a concentration of 1,200 (g/10 a). After the seedlings were raised, the roots of four seedlings were evenly cut to 2 cm, and the seedlings were transplanted into a pot simulating the state of paddy field. After three weeks from the transplantation into the pot simulating the state of paddy field, the plant bodies were harvested, and the dry weights of the aerial part and the root part, and the tillering number were measured. The various treatment conditions employed upon raising the seedlings, and the measurement values obtained after 3 weeks from the transplantation into paddy field pot are presented in Table 8.

TABLE 8

Examination of rice that has been treated upon raising seedlings and transplanted into paddy field pot after raising

| Concentration of 5-aminolevulinic acid hydrochloride treated upon raising seedlings (mg/10a) | Concentration of inabenfide treated upon raising seedlings (g/10a) | Fresh weight of shoots (g) | Dry weight of shoots (g) | Dry weight of roots (g) | Average tillering number per plant body | Degree of sturdiness (dry weight/height for shoots) (g/cm) |
|---|---|---|---|---|---|---|
| 0 | 0 | 10.0 | 2.5 | 0.7 | 3.7 | 0.039 |
| 120 | 0 | 14.1 | 3.2 | 1.0 | 6.7 | 0.052 |
| 0 | 1200 | 15.8 | 3.6 | 1.1 | 8.0 | 0.060 |
| 120 | 1200 | 18.6 | 4.3 | 1.5 | 8.3 | 0.065 | n = 3

As shown in Table 8, promoted growth of plants in the paddy field pot after transplantation was observed, when 5-aminolevulinic acid hydrochloride and inabenfide, which is a gibberellin biosynthesis inhibitor, were used in combination upon raising the seedlings, as compared to the case where the components were used individually. Therefore, the effect of improving the growth of rice seedlings provided by 5-aminolevulinic acid hydrochloride and a gibberellin biosynthesis inhibitor was recognized, and it was found that a combination of these components was useful as an agent for improving seedling growth.

The invention claimed is:

1. An agent for improving the growth of rice seedlings comprising, as active ingredients:
   5-aminolevulinic acid or a salt thereof, and
   60 to 600,000 parts by weight of at least one gibberellin biosynthesis inhibitor, based on 100 parts by weight of the 5-aminolevulinic acid or salt thereof,
   wherein the at least one gibberellin biosynthesis inhibitor is selected from the group consisting of trinexapac-ethyl, paclobutrazol, and prohexadione calcium salt.

2. The agent according to claim 1, wherein the gibberellin biosynthesis inhibitor is trinexapac-ethyl.

3. The agent according to claim 1, wherein the gibberellin biosynthesis inhibitor is paclobutrazol.

4. The agent according to claim 1, wherein the gibberellin biosynthesis inhibitor is prohexadione calcium salt.

5. The agent according to claim 1, comprising 600 to 600,000 parts by weight of the at least one gibberellin biosynthesis inhibitor, based on 100 parts by weight of the 5-aminolevulinic acid or salt thereof.

6. A method for improving the growth of rice seedlings, comprising:
   treating rice seedlings with 5-aminolevulinic acid or a salt thereof, and
   treating rice seedlings with 60 to 600,000 parts by weight of at least one gibberellin biosynthesis inhibitor, based on 100 parts by weight of the 5-aminolevulinic acid or salt thereof,
   wherein the at least one gibberellin biosynthesis inhibitor is selected from the group consisting of trinexapac-ethyl, paclobutrazol, and prohexadione calcium salt.

7. The method according to claim 6, wherein the treatment with 5-aminolevulinic acid or a salt thereof and the treatment with the gibberellin biosynthesis inhibitor are carried out simultaneously.

8. The method according to claim 6, wherein the gibberellin biosynthesis inhibitor is trinexapac-ethyl.

9. The method according to claim 8, comprising treating the rice seedlings with 600 to 600,000 parts by weight of trinexapac-ethyl, based on 100 parts by weight of the 5-aminolevulinic acid or salt thereof, and 0.625 to 2.5 g of trinexapac-ethyl per 10 ares.

10. The method according to claim 6, wherein the gibberellin biosynthesis inhibitor is paclobutrazol.

11. The method according to claim 10, comprising treating the rice seedlings with 600 to 600,000 parts by weight of paclobutrazol, based on 100 parts by weight of the 5-aminolevulinic acid or salt thereof, and 36 to 180 g of paclobutrazol per 10 ares.

12. The method according to claim 6, wherein the gibberellin biosynthesis inhibitor is prohexadione calcium salt.

13. The method according to claim 12, comprising treating the rice seedlings with 600 to 600,000 parts by weight of prohexadione calcium salt, based on 100 parts by weight of the 5-aminolevulinic acid or salt thereof, and 7.5 to 30 g of prohexadione calcium salt per 10 ares.

14. The method according to claim 6, comprising treating the rice seedlings with 600 to 600,000 parts by weight of the at least one gibberellin biosynthesis inhibitor, based on 100 parts by weight of the 5-aminolevulinic acid or salt thereof.

15. The method according to claim 14, comprising treating the rice seedlings with from 1 to 1000 mg of the 5-aminolevulinic acid or salt thereof.

* * * * *